(12) United States Patent
Balduf

(10) Patent No.: US 9,206,108 B2
(45) Date of Patent: Dec. 8, 2015

(54) USE OF A FEED COMPOSITIONS IN PREPARATION OF METHACRYLIC ACID BY OXIDATION

(75) Inventor: Torsten Balduf, Pfungstadt (DE)

(73) Assignee: EVONIK ROEHM GMBH, Darmstadt (DE)

( * ) Notice: Subject to any disclaimer, the term of this patent is extended or adjusted under 35 U.S.C. 154(b) by 218 days.

(21) Appl. No.: 12/598,513

(22) PCT Filed: Feb. 25, 2008

(86) PCT No.: PCT/EP2008/052224
§ 371 (c)(1),
(2), (4) Date: Nov. 2, 2009

(87) PCT Pub. No.: WO2008/145416
PCT Pub. Date: Dec. 4, 2008

(65) Prior Publication Data
US 2010/0120949 A1   May 13, 2010

(30) Foreign Application Priority Data
May 25, 2007 (EP) .................................... 07010479

(51) Int. Cl.
*C07C 51/23* (2006.01)
*B01J 4/00* (2006.01)
*C07C 51/25* (2006.01)
*C07C 67/08* (2006.01)

(52) U.S. Cl.
CPC ............... *C07C 51/23* (2013.01); *B01J 4/008* (2013.01); *C07C 51/252* (2013.01); *C07C 67/08* (2013.01); *B01J 2219/0004* (2013.01); *B01J 2219/00006* (2013.01)

(58) Field of Classification Search
CPC .......... B02J 4/008; C07C 51/23; C07C 67/08; C07C 51/252; C07C 57/04; C07C 69/54
USPC .................................................. 562/537, 538
See application file for complete search history.

(56) References Cited

U.S. PATENT DOCUMENTS

| | | | |
|---|---|---|---|
| 4,012,449 A * | 3/1977 | Shikakura et al. | 568/471 |
| 4,127,603 A * | 11/1978 | Bljumberg et al. | 562/533 |
| 4,147,721 A | 4/1979 | Leacock | |
| 4,147,884 A | 4/1979 | Sheng et al. | |
| 4,652,673 A | 3/1987 | Matsumoto et al. | |
| 4,962,133 A | 10/1990 | Chromecek et al. | |
| 5,276,178 A * | 1/1994 | Onodera et al. | 562/537 |
| 5,338,798 A | 8/1994 | Drzewinski | |
| 6,214,942 B1 | 4/2001 | Siol et al. | |
| 6,265,028 B1 | 7/2001 | Zhao et al. | |
| 6,469,202 B2 | 10/2002 | Nakahara et al. | |
| 2002/0188151 A1 | 12/2002 | Inoue et al. | |
| 2003/0069327 A1 | 4/2003 | Walz et al. | |
| 2003/0216587 A1 | 11/2003 | Au et al. | |

FOREIGN PATENT DOCUMENTS

| | | |
|---|---|---|
| DE | 102 33 685 | 2/2004 |
| EP | 0 590 724 | 4/1994 |
| EP | 0 608 917 A1 | 8/1994 |
| EP | 0 417 606 | 4/1995 |
| EP | 0 886 658 | 12/1998 |
| EP | 0 970 993 | 1/2000 |
| EP | 1 254 887 | 11/2002 |
| JP | 55-124734 | 9/1980 |
| JP | 60-60111 | 4/1985 |
| JP | 1-157930 | 6/1989 |
| JP | 5-179054 | 7/1993 |
| JP | 10-120861 | 5/1998 |
| JP | 2001-64471 | 3/2001 |

(Continued)

OTHER PUBLICATIONS

U.S. Appl. No. 12/598,438, filed Nov. 2, 2009, Balduf.
U.S. Appl. No. 12/597,540, filed Oct. 26, 2009, Balduf.
Office Action issued Jan. 4, 2013 in Japanese Application No. 2010-509755 (English Translation).
European Office Action Issued Mar. 22, 2013 in Patent Application No. 07 010 479.9.
U.S. Appl. No. 14/240,547, filed Feb. 24, 2014, Balduf, et al.
U.S. Appl. No. 14/129,811, filed Dec. 27, 2013, Koestner, et al.
U.S. Appl. No. 14/342,116, filed Feb. 28, 2014, Schaefer, et al.
Korean Office Action issued Apr. 6, 2015 in Patent Application No. 10-2009-7024425 (with Partial English Translation).
Office Action issued Oct. 28, 2014 in Korean Patent Application No. 10-2009-7024425 with English language translation.

(Continued)

*Primary Examiner* — Peter D Mulcahy
(74) *Attorney, Agent, or Firm* — Oblon, McClelland, Maier & Neustadt, L.L.P.

(57) ABSTRACT

The invention relates to a process for production of at least one $C_4$ oxidation product, comprising the steps: a) providing a feed composition comprising at least two feed compounds selected from tert-butyl alcohol, methyl tert-butyl ether and isobutylene; b) subjecting the feed composition to a catalytic reaction zone comprising at least one oxidation stage and obtaining a reaction phase comprising the $C_4$ oxidation product, to a $C_4$ oxidation product obtainable therefrom, to an apparatus for production of at least one $C_4$ oxidation product, a process carried out in the apparatus, to a methacrylic acid, to a polymer comprising methacrylic acid and process for production thereof, to methyl methacrylate and a process for production thereof, to a methacrylate ester and a process for production thereof, to a polymer comprising at least one of methacrylic acid, methyl methacrylate and a methacrylate ester and a process for production thereof, to a composition comprising at least one of methacrylic acid, methyl methacrylate, a methacrylate ester and a polymer comprising at least one of methacrylic acid, methyl methacrylate and a methacrylate ester, to chemical products, and to the use of at least one of methacrylic acid, methyl methacrylate, a methacrylate ester, a polymer comprising at least one of methacrylic acid, methyl methacrylate and a methacrylate ester and a composition comprising at least one of these in chemical products.

14 Claims, 1 Drawing Sheet

(56) References Cited

FOREIGN PATENT DOCUMENTS

| | | |
|---|---|---|
| JP | 2001-122805 | 5/2001 |
| JP | 2003-192627 | 7/2003 |
| JP | 2001-122805 A | 5/2011 |
| KR | 1995-0006522 B1 | 6/1995 |
| WO | WO 02/31426 A1 | 4/2002 |

OTHER PUBLICATIONS

Office Action issued Apr. 3, 2009 in European Patent Application No. 07 010 479.9.

Sebastian Engell, et al., "Continuous-Discrete Interactions in Chemical Processing Plants", Proceedings of the IEEE, vol. 88, No. 7, Jul. 7, 2000, XP11044393, pp. 1050-1068.

* cited by examiner

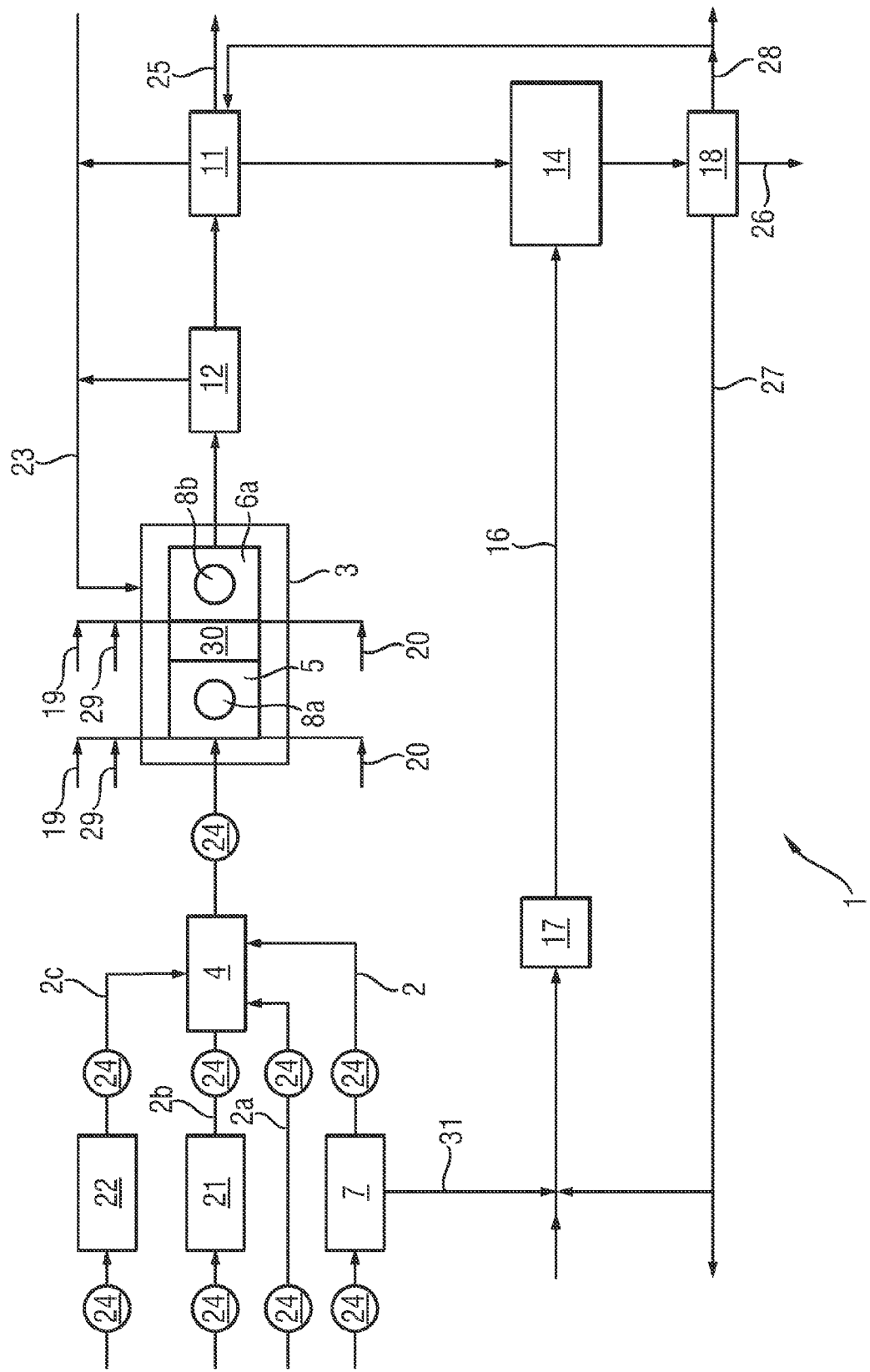

USE OF A FEED COMPOSITIONS IN PREPARATION OF METHACRYLIC ACID BY OXIDATION

The invention in general relates to a process for production of at least one $C_4$ oxidation product, to a $C_4$ oxidation product obtainable therefrom, to an apparatus for production of at least one $C_4$ oxidation product, to a process carried out in the apparatus, to methacrylic acid, to methyl methacrylate and a process for production thereof, to a methacrylate ester and a process for production thereof, to a polymer comprising at least one of methacrylic acid, methyl methacrylate and a methacrylate ester and a process for production thereof, to a composition comprising at least one of methacrylic acid, methyl methacrylate, a methacrylate ester and a polymer comprising at least one of methacrylic acid, methyl methacrylate and a methacrylate ester, to chemical products, and to the use of at least one of methacrylic acid, methyl methacrylate, a methacrylate ester, a polymer comprising at least one of methacrylic acid, methyl methacrylate and a methacrylate ester and a composition comprising at least one of these in chemical products.

Methacrylic acid (MAA) and polymethacrylic acid (PMAA) are important industrial products with applications in, for example thickening agents, suspending agents, flocculants and resins, among other applications. A significant proportion of industrially produced MAA is, however, used in the production of its esters, in particular of methyl methacrylate and polymethyl methacrylate.

Methyl methacrylate (MMA) is a valuable industrial product with estimated current worldwide production of 3.3 million metric tons per year. It is principally used in the production of polymethyl methacrylate (PMMA) acrylic plastics. PMMA materials have high transparency, weathering stability and resistance to scratching, as well as being easily moulded, light and having high breaking strength. They are used, among other applications, in automobile and transportation systems, in optics and communications, in medical technology and in construction and lighting.

Other important applications of methyl methacrylate are in the production of co-polymers such as the co-polymer methyl methacrylate-butadiene-styrene (MBS), which is used as a modifier for PVC; in paints and varnishes such as waterborne coatings, for example latex house paint; in adhesives; and more recently in plates that keep light spread evenly across LCD computer and TV screens, for example in flat screens, and in contact lenses. Methyl methacrylate is also used in preparation of corrosion casts of anatomical organs, such as coronary arteries of the heart.

Special methacrylate ester derivatives, for example, of alkyl and aryl alcohols, hydroxyalcohols, polyethylene glycols, quaternary ammonium derivatives and aminoalcohols, among others, have applications in, for example, contact lenses, coatings, drug delivery, controlled release of active substances, adhesives, lubricants, flow improvers, compatibility agents for polymer blends, bonding agents, food packaging, lacquers and PVC-free underseal compounds for automobile manufacture.

Various processes are known in the art for preparing methyl methacrylate, such as those based on hydrolysis of acrylonitrile or on the reaction of acetylene, carbon monoxide and an alcohol in the presence of a nickel carbonyl complex. An acetone cyanohydrin (ACH) route, with acetone and hydrogen cyanide as raw materials, is also applied. A disadvantage of these routes is the extremely high toxicity of nickel carbonyl and acetone cyanohydrin. An alternative route is the esterification of methacrylic acid with methanol.

So-called oxyesterification processes are also known, for example from U.S. Pat. No. 4,060,545, U.S. Pat. No. 4,014,925, U.S. Pat. No. 3,925,463, U.S. Pat. No. 3,758,551, U.S. Pat. No. 5,670,702, U.S. Pat. No. 6,107,515 where oxidation of propylene, isobutylene, acrolein or methacrolein and esterification of the oxidised product to an acrylate or a methacrylate takes place in the same reactor.

According to a widely used industrial process for preparation of methacrylic acid, isobutylene or tert-butyl alcohol (TBA) is oxidised on suitable catalysts, first to methacrolein and then further to methacrylic acid. Either the methacrolein or the methacrylic acid is then esterified with methanol, in the case of methacrolein in an oxyesterification reaction, to form the desired methacrylate. The isobutylene used in this process is often obtained by splitting of methyl tert-butyl ether (MTBE) to provide principally isobutylene and methanol, together with side products including dimethyl ether and TBA, as well as unreacted MTBE. Isobutylene can also be obtained from splitting of ethyl tert-butyl ether (ETBE) to afford principally isobutylene and ethanol, together with side products. It has long been known, for example from EP 0 068 785 A1, that the presence of side products in the low-boiling isobutylene fraction is problematic for subsequent reactions of the isobutylene, in particular in oxidation to methacrylic acid. The isobutylene fraction must therefore generally be purified by removing the side products, as well as methanol or ethanol, before it can be subjected to oxidation to methacrylic acid. Such purification is generally time-consuming and expensive, requiring a number of purification steps. It would thus be advantageous to be able to reduce the extent of purification of isobutylene which is to be oxidised to methacrolein and/or methacrylic acid, without detrimental effects on the oxidation reaction or on the yield of oxidation product(s) of isobutylene.

U.S. Pat. No. 4,652,673 discloses that the presence of isobutylene or TBA in the methacrolein phase in vapour phase oxidation of methacrolein over specific catalysts increases the yield of methacrylic acid. This document is, however, silent regarding the presence of MTBE, ETBE or TBA in an isobutylene phase which is to be oxidised to methacrolein.

An object of the present invention was thus to overcome the problems associated with the prior art.

A particular object was to provide an improved and more economical process for preparation of methacrylic acid and methyl methacrylate. It was also desired to avoid the use of highly toxic chemicals in the production of methyl methacrylate.

A particular object of the invention was to reduce the purification effort required for isobutylene before its oxidation, in particular for isobutylene obtained from splitting of MTBE, while maintaining economically advantageous yields of methacrolein and/or of methacrylic acid.

Another object of the present invention is to provide a method and an apparatus for a more efficient use of methanol in the production of methacrylic acid and methyl methacrylate.

A contribution to the solution of at least one of the above problems is made by the subject matter of the category-forming claims. The sub-claims dependent on the category-forming claims describe preferred embodiments according to the invention.

A contribution to solving the above objects is made by a process according to the present invention for production of at least one $C_4$ oxidation product, comprising the steps:

a) providing a feed composition comprising at least two feed compounds selected from isobutylene, tert-butyl alcohol, methyl tert-butyl ether, ethyl tert-butyl ether;

b) subjecting the feed composition to a catalytic reaction zone comprising at least one oxidation stage and obtaining a reaction phase comprising at least one $C_4$ oxidation product.

The feed composition may also comprise methanol as feed compound. The feed composition can comprise one, two, three, four or all feed compounds mentioned but preferably comprises two, three or four feed compounds selected from isobutylene, tert-butyl alcohol, methyl tert-butyl ether, ethyl tert-butyl ether and methanol, whereby a feed composition comprising isobutylene and tert-butyl alcohol or isobutylene and methyl tert-butyl ether, or isobutylene, methanol and tert-butyl alcohol, or isobutylene, methanol and methyl tert-butyl ether, or isobutylene and ethyl tert-butyl ether, or a feed composition comprising tert-butyl alcohol and methyl tert-butyl ether, or tert-butyl alcohol, methanol and methyl tert-butyl ether or tert-butyl alcohol and ethyl tert-butyl ether is preferred according to the invention. In one embodiment it is preferred that the feed compound further comprises less than 70 mol %, preferably less than 60 mol %, preferably less than 50 mol %, more preferably less than 40 mol %, even more preferably less than 30 mol %, yet more preferably less than 20 mol %, more preferably less than 10 mol % methacrolein, based on the hydrocarbons in the feed composition. In another embodiment, it is preferred that the feed composition does not comprise methacrolein.

It is preferred in the process according to the invention that in step b) the feed composition comprises at least one of the feed compounds as main feed compound and at least one of the other feed compounds as further feed compound. An upper limit for the total amount of further feed compound in the feed composition is preferably about 50 wt. %, based on the total weight of the feed compounds in the feed composition, whereby the at least one further feed compound is preferably comprised in a range from 0.0005 to 10 wt. %, preferably from 0.0008 to 8 wt. %, more preferably from 0.001 to 7 wt. %, yet more preferably from 0.001 to 6 wt. %, more preferably from 0.001 to 5 wt. %, more preferably from 0.005 to 4 wt. %, more preferably from 0.01 to 3 wt. %, even more preferably from 0.1 to 2.7 wt. %, more preferably from 0.5 to 2.5 wt. %, based on the total weight of the feed compounds in the feed composition.

It is preferred in one aspect of the process according to the invention that in step b) the feed composition has isobutylene and/or TBA as main feed compound and a content of not less than 5 ppm, preferably not less than 6 ppm, preferably not less than 7 ppm, preferably not less than 8 ppm, more preferably not less than 9 ppm and yet more preferably not less than 10 ppm of at least one of the further feed compounds. In another preferred aspect of the process according to the invention, the feed composition has TBA as main feed compound and a content of not less than 5 ppm, preferably not less than 6 ppm, preferably not less than 7 ppm, preferably not less than 8 ppm, more preferably not less than 9 ppm and yet more preferably not less than 10 ppm of at least one further feed compound.

In a preferred embodiment of the process according to the invention, the feed composition provided in step a) is obtained by splitting of MTBE or of ETBE. MTBE is widely used as feedstock for isobutylene and splitting of MTBE is well known in the art. Splitting of ETBE can be achieved as for MTBE. Thus, splitting of MTBE or ETBE can occur by any suitable means which are known to the skilled person. Suitable catalysts and reaction conditions are described, for example, in EP 1 149 814 A1, WO 04/018393 A1, WO 04/052809 A1; Ullmann's Encyclopedia of Industrial Chemistry, 5$^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, 5$^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein. The disclosures of these references are hereby incorporated by reference and form part of the disclosure of the present invention.

The two main products of MTBE splitting are isobutylene and methanol. The two main products of ETBE splitting are isobutylene and ethanol. Further components which are often also present in the splitting phase resulting from the MTBE splitting are, among others, dimethyl ether, tert-butyl alcohol, methyl sec-butyl ether (MSBE) and unreacted MTBE. Further components present in the splitting phase resulting from the ETBE splitting can be diethyl ether, tert-butyl alcohol, ethyl sec-butyl ether (ESBE) and unreacted ETBE.

In one aspect of the process according to the invention, the splitting phase may be provided directly as feed composition without purification. In a preferred aspect of the process according to the invention, the splitting phase obtained from an MTBE or ETBE splitting reaction is subjected to at least one of at least partial separation and/or purification before being used as feed composition. Suitable purification and separation processes are described, for example, in EP 1 149 814 A1, WO 04/018393 A1 and WO 04/052809 A1. In a further preferred aspect of the process according to the invention, at least a part preferably at least 90%, preferably at least 92%, more preferably at least 95%, yet more preferably at least 97%, even more preferably at least 98%, more preferably at least 99% of the methanol or ethanol obtained in the splitting reaction is separated from the splitting phase to form a methanol phase or an ethanol phase and a depleted splitting phase which is depleted in methanol or ethanol.

The depleted splitting phase, which comprises isobutylene as main component, can be optionally purified and provided as feed composition. Suitable separation and purification methods are known to the person skilled in the art and preferably comprise at least one of distillation, extraction, adsorption, absorption, phase separation, membrane separation, chromatography or washing, preferably at least one of distillation and extraction, preferably at least one distillation and at least one extraction. It is preferred that in this process step at least one of methanol, MTBE, MSBE, ethanol, ESBE and ETBE is at least partially separated from the isobutylene phase. Separated MTBE and ETBE can be optionally purified and at least partially recycled to the splitting reaction. The separated methanol phase can be optionally purified and removed or be recycled to a further process step, for example a later esterification process step where it reacts with methacrylic acid to form methyl methacrylate.

If TBA is to be comprised as feed compound in the feed composition, this may be obtained commercially, prepared from isobutylene and water, for example from a source of isobutylene as described above, or alternatively obtained from propene oxide production via hydroperoxydation as described in U.S. Pat. No. 5,424,458, U.S. Pat. No. 5,436,376, U.S. Pat. No. 5,274,138, Ullmans encyclopedia, 5$^{th}$ Edition, Vol. A4, p. 492 and references cited therein.

Any or all of the feed compounds can be optionally purified by suitable techniques known to the skilled person, such as those mentioned above, before being provided to the feed composition. A particular advantage of the present invention is that a lesser degree of purification of the feed composition is possible, resulting in energy and time savings.

To the feed composition is preferably added a source of oxygen, which source is not limited and can be any suitable source of oxygen ($O_2$) such as peroxide, molecular oxygen or oxygen-enriched or oxygen-comprising gas, whereby air is preferred as oxygen source for economic reasons. An $O_2$ source is understood here to be any compound or composition that comprises or liberates $O_2$. The amount of molecular oxygen provided as $O_2$ or as $O_2$ source is preferably from about 0.5 to about 20 moles, preferably from about 1 to about 10 moles $O_2$ per mole of isobutylene and/or TBA, more preferably from about 1 to about 5 moles $O_2$ per mole of isobutylene and/or TBA, more preferably from about 1 to about 3 moles $O_2$ per mole of isobutylene and/or TBA, more preferably from about 1 to about 2 moles $O_2$ per mole of isobutylene and/or TBA. Water and/or water vapour (steam) can also be added to the feed composition. If water and/or water vapour is added to the feed composition it is preferred that from about 1 to about 20 moles, preferably from about 1 to about 15 moles, preferably from about 1 to about 10 moles, more preferably from about 1 to about 8 moles of water and/or water vapour is added to the feed composition, per mole of isobutylene and/or TBA. The molar ratio of isobutylene:oxygen as $O_2$ or $O_2$ equivalent:water and/or water vapour at the start of step b) is preferably about 1:2:1. It may not be preferred to comprise water and/or water vapour in the feed composition at the start of step b) to the extent that TBA is comprised therein. It is further preferred that at least one diluent is added to the feed composition, which diluent can comprise inorganic or organic solvent or a gas, preferably at least one diluent gas which is inert under the reaction conditions, preferably selected from nitrogen, argon, carbon dioxide and carbon monoxide, whereby nitrogen gas and/or carbon dioxide, preferably carbon dioxide recycled from a combustion unit, preferably a catalytic or thermal combustion unit, is preferred as diluent gas.

According to the process according to the invention, in step b) the feed composition is preferably subjected to oxidation to obtain a reaction phase comprising at least one $C_4$ oxidation product. The oxidation is preferably a catalytic oxidation, preferably a gas phase catalytic oxidation. Suitable reaction conditions for gas phase catalytic oxidation are, for example, temperatures of from about 250° C. to about 450° C., preferably from about 250° C. to about 390° C. and pressures of from about 1 atm. to about 5 atm. The space velocity can vary from about 100 to about 6000 hr$^{-1}$ (NTP) and preferably from about 500 to about 3000 hr$^{-1}$. Oxidation, for example gas phase catalytic oxidation, of $C_4$ feeds such as isobutylene to methacrolein and/or methacrylic acid, as well as catalysts therefor, are well known in the literature, for example from U.S. Pat. No. 5,248,819, U.S. Pat. No. 5,231,226, U.S. Pat. No. 5,276,178, U.S. Pat. No. 6,596,901 B1, U.S. Pat. No. 4,652,673, U.S. Pat. No. 6,498,270, U.S. Pat. No. 5,198,579, U.S. Pat. No. 5,583,084.

The at least one oxidation product formed in the catalytic reaction zone in step b) can be any oxygen-comprising product based on a $C_4$ feed compound, preferably at least one $C_4$ oxidation product such as a $C_4$ alcohol, a $C_4$ aldehyde or a $C_4$ acid, whereby the at least one $C_4$ oxidation product is preferably at least one of methacrolein and methacrylic acid. If methanol is comprised in the feed composition, methyl methacrylate may also be formed in the catalytic reaction zone.

In a preferred embodiment of the process according to the invention, the oxidation in step b) takes place in a single oxidation stage. If the process according to the invention comprises a single oxidation stage in step b), it is preferred that the resulting oxidation phase comprises methacrylic acid as main component.

In another preferred embodiment of the process according to the invention, the oxidation in step b) takes place in at least two separate oxidation stages, preferably in two separate oxidation stages. These at least two oxidation stages can be oxidation stages within a same area of the catalytic reaction zone, for example if the catalytic reaction zone is in the form of one or more reactors, a first oxidation stage can be in a first oxidation area in a reactor and a further oxidation stage can be in a further oxidation area downstream of the first oxidation area in the same reactor, or a first oxidation stage can be in a first reactor and a further oxidation stage can be in a further reactor. It is preferred that the first oxidation stage and the further oxidation stage are at different temperatures, and preferably that the first oxidation stage and the further oxidation stage are separated by an intermediate area at a different temperature to that of either of the first and further oxidation stages.

It is further possible that one or both of the oxidation stages are gas phase or liquid phase oxidation stages. It is also possible that one oxidation stage is a gas phase oxidation stage and the other oxidation stage is a liquid phase oxidation stage. In a preferred aspect of the process according to the invention, the first and second oxidation stages are gas phase oxidation stages. In another preferred aspect of the process according to the invention, the first oxidation stage is a gas phase oxidation stage and the second oxidation stage is a liquid phase oxidation stage.

In an embodiment of the process according to the invention where the oxidation takes place in at least two separate oxidation stages, it is possible that a quenching step takes place between at least two of the at least two separate oxidation stages. This quenching step is preferably a quenching step enabling separation of methacrolein. This embodiment can be particularly preferred if a second or further oxidation stage is a liquid phase oxidation stage, or if a second or further oxidation stage is to be combined with a further reaction stage, for example to form a combined liquid phase oxidation-esterification stage. Quenching of this type can be carried out by any suitable method known to the skilled person. Suitable methods are described, for example, in DE 34 41 207 A1 and in JP 60087241.

In a preferred aspect of the process according to the invention comprising a two-stage oxidation, in a first oxidation stage the amount of $O_2$ provided is preferably from about 0.5 to about 10 moles, preferably from about 1 to about 5 moles, more preferably from about 1 to about 3 moles, preferably from about 1 to about 2 moles $O_2$ per mole of isobutylene and/or TBA, and a preferred amount of water and/or water vapour is in the range from 0 to about 20 moles, preferably from 0 to about 10 moles, more preferably from 0 to about 5 moles $H_2O$ per mole of isobutylene and/or TBA, whereby a molar ratio $O_2$:isobutylene and/or TBA:water and/or water vapour of about 2:1:0 is preferred if mainly TBA is provided as $O_4$ feedstock in the feed composition and about 2:1:1 if mainly isobutylene is provided as $O_4$ feedstock in the feed composition. In a second oxidation stage the amount of $O_2$ provided is preferably from about 0.5 to about 10 moles, preferably from about 1 to about 5 moles, more preferably from about 1 to about 3 moles $O_2$ per mole of isobutylene and/or TBA, and a preferred amount of water and/or water vapour is in the range from about 1 to about 20 moles, preferably from about 1 to about 10 moles, more preferably from about 2 to about 8 moles, yet more preferably from about 4 to about 5 moles $H_2O$ per mole of isobutylene and/or TBA, whereby a preferred molar ratio $O_2$:isobutylene and/or TBA: water and/or water vapour in a second oxidation stage is in the range of about 2:1:2-6, preferably in the range of about 2:1: 3-5, based on the number of moles isobutylene and/or TBA provided in the feed composition in the first oxidation stage.

If the oxidation takes place in at least two separate oxidation stages in the process according to the invention, the feed composition is preferably provided before the first oxidation stage. In this embodiment of the process according to the invention, the feed composition is subjected to the first oxidation stage to form a first $C_4$ oxidation phase of the first oxidation stage. The first $C_4$ oxidation phase is optionally quenched and then subjected to at least one further oxidation stage, preferably to a second oxidation stage.

It is preferred in the process according to the invention where the oxidation takes place in at least two separate oxidation stages that the main product in the $C_4$ oxidation phase of the first oxidation stage is methacrolein and the main product in a further $C_4$ oxidation phase of a further oxidation stage is methacrylic acid. The presence in the feed composition of at least two feed compounds selected from isobutylene, TBA, ETBE and MTBE results in a yield of methacrylic acid which is increased compared to the expected yield of methacrylic acid if the same reaction is carried out on either isobutylene or TBA in the absence of at least one of the further feed compounds. The presence of methanol in the feed composition results in a comparably slightly reduced yield of methacrylic acid, which is compensated by the formation of methyl methacrylate. This can be advantageous if the methacrylic acid is intended for conversion into methyl methacrylate.

The process according to the invention preferably further comprises the step c) working up the at least one $C_4$ oxidation product.

In step c) of the process according to the invention, the oxidation phase is preferably subjected to at least one of quenching and/or purification to separate methacrolein and/or methacrylic acid, and to remove unreacted feed composition compounds and/or undesired side products arising from the reaction or reactions in the catalytic reaction zone. The quenching can be carried out by any suitable quenching process known to the skilled person, as described for example in Offenlegungsschrift DE 21 36 396, EP 297 445 A2, EP 297 788 A2, JP 01193240, JP 01242547, JP 01006233, US 2001/0007043 A1, U.S. Pat. No. 6,596,901 B1, U.S. Pat. No. 4,956,493, U.S. Pat. No. 4,618,709 B1, U.S. Pat. No. 5,248,819, whose disclosure concerning quenching of acrylic and methacrylic acids is hereby incorporated and forms part of the present disclosure. Preferred quenching agents are water and organic solvents such as, for example, aromatic or aliphatic hydrocarbons, or mixtures of at least two thereof, whereby preferred organic solvents have relatively low vapour pressure under the quenching conditions, such as heptane, toluene or xylene. The purification can be carried out by any suitable purification means known to the skilled person, such as by distillation, crystallisation, extraction, absorption or precipitation, preferably by crystallisation. Such purification techniques are well known in the art, for example in DE 100 39 025 A1, US 2003/0175159, DE 100 36 881 A1, EP 297 445 A2, JP 01193240, JP 01242547, JP 01006233, U.S. Pat. No. 6,596,901 B1, U.S. Pat. No. 6,646,161 B1, U.S. Pat. No. 5,248,819, U.S. Pat. No. 4,618,709 B1, and references cited therein. Reference is hereby explicitly made to these disclosures concerning purification and they form part of the disclosure of the present invention.

It is preferred that in a quenching step and/or in a purification step unreacted methacrolein is separated. The separated methacrolein can be recycled to the catalytic reaction zone, whereby if the catalytic reaction zone comprises more than one oxidation stage the separated methacrolein is preferably recycled to a further oxidation stage, preferably to the second oxidation stage of a catalytic reaction zone comprising two oxidation stages. In this way, the separated methacrolein can be further subjected to oxidation, thereby leading to increased efficiency of the overall process and increased yields of methacrylic acid. Methacrylic acid produced according to the process according to the invention can be at least partially collected, or it can be conducted to further reactions or processes. At least one polymerisation inhibitor is preferably added to the methacrylic acid. Thus, manipulation of methacrylic acid in at least one process step, in particular in any process step taking place at increased temperature, preferably takes place in the presence of a polymerisation inhibitor.

According to the invention, it is possible that either or both of steps a) and b) occur at least partially in liquid phase and/or in the gas phase. Thus it is possible that both steps occur at least partially in liquid phase, that both steps occur at least partially in the gas phase, or that at least one step occurs at least partially in the liquid phase and the other step occurs at least partially in the gas phase. In a preferred aspect of the invention, both of steps a) and b) occur at least partially in the gas phase. It is particularly preferred according to the process according to the invention that at least step b) occurs at least partially in the gas phase. In an embodiment of the process according to the invention wherein in step b) the oxidation takes place in two separate oxidation stages, it is possible that one or both of the oxidation stages are gas phase or liquid phase oxidation stages. It is also possible that one oxidation stage is a gas phase oxidation stage and the other oxidation stage is a liquid phase oxidation stage. In a preferred aspect of the process according to the invention, the first and second oxidation stages are gas phase oxidation stages. In another preferred aspect of the process according to the invention, the first oxidation stage is a gas phase oxidation stage and the second oxidation stage is a liquid phase oxidation stage. If the second oxidation stage is a liquid phase oxidation stage it is also possible that this second oxidation stage is combined into a combined liquid phase oxidation-esterification stage.

If step b) occurs at least partially in the gas phase, it is preferred or even necessary that a quenching step as described above is carried out prior to purification of the oxidation phase.

The invention also relates to an apparatus for production of at least one $O_4$ oxidation product, preferably for production of methacrylic acid, comprising:

α) at least two feed supplies; in fluid communication with

β) a catalytic reaction zone;

γ) at least one control unit for controlling the at least two feed supplies.

The at least two feed supplies can be any means suitable for supplying a feed composition to the catalytic reaction zone, for example a reservoir, a pipe, a line, a tube, or the like. The at least two feed supplies should preferably be resistant to elevated and/or decreased temperature and/or pressure, preferably resistant at least to temperatures and pressures as described above for a preferred oxidation reaction. A good temperature and/or pressure resistance is particularly preferred if one or more of the reactions which should take place in the apparatus is a gas phase reaction. The at least two feed supplies are furthermore preferably not reactive with any of the components of the feed composition, nor with any further component such as oxygen or an oxygen equivalent, water and/or water vapour, diluent, which might be added to the feed composition, as mentioned above in connection with the process according to the invention. Any supply which is intended to supply a gaseous phase or composition is preferably maintained at a temperature above the dewpoint temperature of the gas to be supplied. This can be achieved, for example, by heating or by thermally insulating the supply.

In a preferred embodiment of the apparatus according to the present invention, at least one feed supply is preferably in fluid communication with an MTBE and/or ETBE (ethyl tert-butyl ether) splitting unit. The term "in fluid communication" is understood here as meaning that at least one supply is connected with the splitting unit such that a fluid, which can be at least one of a liquid, a gas, a vapour, a supercritical fluid or any other fluid, can flow from the supply to the splitting unit or from the splitting unit to the supply. Splitting units for MTBE and ETBE are well known in the art and form part of the general knowledge of the skilled person, as described, for example, in Ullmann's Encyclopedia of Industrial Chemistry, $5^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, $5^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein.

It is preferred in the apparatus according to the invention that the at least two feed supplies are at least two of
α1) a supply for methyl tert-butyl ether and/or ethyl tert-butyl ether, preferably for methyl tert-butyl ether;
α2) a supply for isobutylene; and
α3) a supply for tert-butyl alcohol.

A supply for methanol may also be comprised. It is also conceivable that at least one feed supply is a supply for at least two feed compounds, for example, a supply for at least two feed compounds present in the effluent of an MTBE or ETBE splitter, such as, for example, isobutylene and methanol, isobutylene and MTBE or ETBE, or isobutylene, methanol and MTBE.

It is possible that any or all of the supplies can be in fluid communication with an MTBE and/or ETBE splitting unit. One or more purifications units can furthermore be comprised in the apparatus according to the invention upstream of, and in fluid communication with, the catalytic reaction zone, for example between an MTBE splitting unit and at least one supply, and/or between at least one supply and the control unit. The apparatus according to the invention may comprise a purification unit for each feed compound. At least one purification unit is preferably a purification unit for isobutylene. Suitable purification units are known to the person skilled in the art and preferably comprise at least one of an extractor, a crystalliser, a column, a distillation device, a rectification device, a membrane, a pervaporation device, an adsorption unit, an absorption unit and a wash device, preferably at least one distillation device and/or extractor.

If methanol or ethanol is to be separated from the effluent of an MTBE or ETBE splitter respectively, such a splitter is preferably in fluid communication with at least one first separation unit for separation of methanol or ethanol from the effluent of the splitter. The separation unit can comprise any means suitable and known to the skilled person for separating methanol or ethanol from the other components comprised in this effluent. Examples of suitable means are an extractor, a crystalliser, a column, a distillation device, a rectification device, a membrane, a pervaporation device, a phase separation device, an absorption device, an adsorption device and a wash device.

It is also possible that one or more feed compounds are added to the feed composition separately from the effluent from an MTBE and/or ETBE splitting unit, either as main source, or as supplementary source, of the respective feed compound in the feed composition. If, for example, tert-butyl alcohol and/or isobutylene are to be added separately in this way, it is preferred according to the invention that the supply for tert-butyl alcohol is in fluid communication with a tert-butyl alcohol evaporator and/or that the supply for isobutylene is in fluid communication with an isobutylene evaporator. Such an arrangement results in a particularly favourable operation of the apparatus, for example enabling a flexible response to changing availability of feedstocks.

In the apparatus according to the invention, the catalytic reaction zone preferably comprises at least one oxidation area. The at least one oxidation area is preferably at least one oxidation area suitable for carrying out oxidation of isobutylene and/or TBA to at least one of methacrolein and methacrylic acid, preferably comprising at least one oxidation catalyst. The at least one oxidation area can be, for example, a multitube reactor such as a tube and shell reactor, a plate reactor or a fluidised bed reactor, whereby a multitube reactor is preferred, preferably a multitube reactor packed with oxidation catalyst. Such reactors are commercially available, for example from MAN DWE GmbH, Deggendorfer Werft, Germany, or from Ishikawajima-Harima Heavy Industries (IHI Corporation from 1 Jul. 2007), Japan, and form part of the general knowledge of the person skilled in the art.

In a preferred embodiment of the apparatus according to the invention, the catalytic reaction zone comprises one oxidation area, preferably one oxidation unit, preferably one oxidation reactor, whereby it is preferred that this oxidation area comprises at least one catalyst, preferably a catalyst capable of oxidation of at least one of isobutylene and TBA to at least one of methacrolein and methacrylic acid, preferably to methacrylic acid.

In another preferred embodiment of the apparatus according to the invention, the catalytic reaction zone, preferably the at least one oxidation unit, comprises at least a first oxidation area and a further oxidation area, preferably a first oxidation area and a second oxidation area. The first oxidation area and the further oxidation area, preferably the first oxidation area and the second oxidation area, can be different oxidation areas in a single reactor, or they can each be in a separate respective reactor, with all reactors being in fluid communication with each other. In an embodiment where the catalytic reaction zone is in the form of one reactor, a first oxidation stage is preferably in a first oxidation area in a reactor and a further oxidation stage is then in a further oxidation area downstream of the first oxidation area in the same reactor. In a preferred aspect, the reactor is a multitube reactor as described above. In this case it is preferred that at least one oxidation catalyst, preferably at least two oxidation catalysts, are provided, preferably in a layered-type fashion, preferably such that a first oxidation stage occurs at at least one upstream catalyst layer and a further oxidation stage at at least one further catalyst layer downstream thereof. Catalyst layers in a same tube can be directly adjacent to each other. It is also possible that at least one catalyst layer is separated from at least one other catalyst layer by at least one intermediate area, for example at least one mixing area or at least one transition area, e.g. at least one transition area between an area with a certain number of tubes and an area with a different number of tubes, or by means of layers of, for example, packing materials or suspending agents which are inert under the reaction conditions. If, in a process where the first oxidation and a further oxidation occur in the gas phase, the first oxidation area and the further oxidation area are in separate reactors, it is preferred that all reactors are multitube reactors. On the other hand, if at least one reactor is a liquid phase reactor, for example a liquid phase oxyesterification reactor, this reactor is preferably not a multitube reactor.

It is additionally preferred that the first oxidation area and the further oxidation area or areas are at different temperatures. It is further preferred that the first and further oxidation areas, in particular if they are at different temperatures with respect to each other, are separated by an intermediate area which is at a different temperature to that of either of the first and further oxidation areas.

It is preferred in the apparatus according to the invention that, if the apparatus comprises a first oxidation area and a further oxidation area, the first oxidation area comprises a first oxidation catalyst and the further oxidation area comprises a further oxidation catalyst, whereby the further oxidation area is preferably a second oxidation area and the further oxidation catalyst is preferably a second oxidation catalyst. The first oxidation catalyst is preferably a catalyst for oxidation of isobutylene to methacrolein, and the further oxidation catalyst, preferably the second oxidation catalyst, is preferably a catalyst for oxidation of methacrolein to methacrylic acid. The first and further catalysts are not particularly limited and are preferably solid catalysts suitable for the respectively preferred oxidation, preferably mixed metal oxide catalysts. Such catalysts are well known in the art, for example as described in JP 58059934, JP 55045617, EP 0 005 769, EP 1 350 566 A2, EP 0 450 596 A2, EP 0 456 837 A1, WO 2001/098247 A2, EP 0 630 879 A1, US 2002/0198406 A1, EP 911 313 A1, U.S. Pat. No. 5,602,280, EP 145 469, U.S. Pat. No. 5,218,146, U.S. Pat. No. 4,365,087, U.S. Pat. No. 5,077,434, U.S. Pat. No. 5,231,226 or US 2003/0004374 A1, U.S. Pat. No. 6,498,270 B1, U.S. Pat. No. 5,198,579, EP 1 595 600 A1, EP 1 052 016 A2, U.S. Pat. No. 5,583,084, and references cited therein, whose disclosure concerning oxidation catalysts is hereby incorporated by reference and forms a part of the disclosure of the present invention. If a first and a further oxidation catalyst are comprised they are preferably arranged in the at least one oxidation area as described above.

If the apparatus according to the invention comprises a first oxidation reactor and at least one further oxidation reactor as described above, it is possible that a quenching unit is provided downstream of a first oxidation reactor and upstream of at least one further oxidation reactor, preferably between the first and second oxidation reactors. This quenching unit preferably serves to transfer at least a part of the reaction phase formed in the first oxidation reactor into a liquid phase, as well as preferably to at least partially separate methacrolein. A quenching unit between the first oxidation reactor and at least one further oxidation reactor is preferred if the first oxidation reactor is a gas phase reactor and the at least one further reactor is a liquid phase reactor. Quenching units suitable for use in the apparatus are preferably those as described, for example, in the references cited above in connection with a quenching process step.

In a preferred aspect of the apparatus of the present invention, at least one supply for at least one $O_2$ source, preferably at least one supply for air, and at least one supply for water and/or steam, are in fluid communication with at least one of the catalytic reaction zone, the at least one control unit and an area of the apparatus which may be upstream of the at least one control unit but which is preferably downstream of at least one control unit and upstream of the catalytic reaction zone. It is preferred according to the invention that the at least one supply for at least one $O_2$ source and the at least one supply for water and/or steam provide respectively at least one $O_2$ source and water and/or steam, directly to the catalytic reaction zone. If the catalytic reaction zone comprises at least a first and a further oxidation area, the apparatus preferably comprises at least one supply for at least one $O_2$ source and at least one supply for water and/or steam for each oxidation area. The apparatus can further comprise a supply for a diluent such as nitrogen, argon and/or carbon dioxide, preferably nitrogen or carbon dioxide, preferably carbon dioxide-comprising recycle gas from a catalytic combustion unit (CCU) or a thermal combustion unit (TCU), preferably from a catalytic combustion unit.

The apparatus according to the invention optionally comprises at least one purification unit in fluid communication with the catalytic reaction zone. The at least one purification unit is preferably suitable for purification of methacrylic acid, preferably for separation of methacrylic acid from water and/or terephthalic acid (TPA), and preferably comprises at least one of a distiller, an absorber, a crystalliser, an extractor, a wash device and a column. It is particularly preferred that the at least one purification unit comprises at least one crystalliser and/or at least one absorber, preferably at least one absorber and at least one crystalliser. It is possible that the at least one first purification unit comprises more than one purification stage. Unreacted methacrolein can be separated here and, if desired, conducted back to the catalytic reaction zone for further reaction. If the purification unit comprises at least a first purification stage and a further purification stage, it is preferred that unreacted methacrolein is at least partially separated in a first purification stage. Suitable purification units are described in the references mentioned above in connection with a process step for purification of methacrylic acid.

In a preferred embodiment of the apparatus according to the invention, at least one quench unit is comprised between and in fluid communication with the catalytic reaction zone and the purification unit. It is preferred that methacrylic acid present in the oxidation phase leaving the catalytic reaction zone is condensed in the quench unit to form a solution comprising methacrylic acid as main oxidation product. Unreacted methacrolein can also be separated in the quench unit and, if desired, conducted back to the catalytic reaction zone for further reaction. Quench units suitable for use in the apparatus are described, for example, in the references cited above in connection with a quenching process step and an intermediate quenching step.

The apparatus according to the invention comprises at least one control unit for controlling the at least two feed supplies. The at least one control unit can be any control unit known to the skilled person and which is suitable for regulating the flow and/or the amount of at least one feed compound, preferably of all feed compounds, preferably of at least one feed compound in gaseous or vapour form, in one or more of the at least two feed supplies. The control unit preferably serves to regulate the flow, for example the flow rate, and/or the constitution of the feed composition before entry into the catalytic reaction zone. Examples of suitable control units are valves, regulators, mixers, taps, tubes, pipes and the like.

The invention also relates to a process as described above, wherein said process is performed in an apparatus as described above.

The invention also relates to methacrylic acid obtainable by a process as described above.

The generally optionally but sometimes necessarily quenched and/or purified oxidation phase comprising at least one oxidation product, preferably methacrylic acid, as described above, can be optionally subjected to esterification in a further process step.

The invention thus also relates to a process for preparation of methyl methacrylate, comprising the steps:
a) providing a feed composition comprising at least two feed compounds selected from isobutylene, tert-butyl alcohol, methyl tert-butyl ether, ethyl tert-butyl ether and methanol;
b) subjecting the feed composition to a catalytic reaction zone comprising at least one oxidation stage and obtaining a reaction phase comprising at least one $C_4$ oxidation product selected from methacrolein and methacrylic acid;
c) subjecting the reaction phase obtained in b) to esterification.

The means of carrying out the esterification in step c) is not particularly limited. The esterification can be carried out, for example, as described in U.S. Pat. No. 6,469,202, JP 1249743, EP 1 254 887 A1, U.S. Pat. No. 4,748,268, U.S. Pat. No. 4,474,981 or U.S. Pat. No. 4,464,229 whose disclosures concerning esterification of acrylic and methacrylic acids are hereby incorporated and form part of the present disclosure.

Methanol is also provided to the esterification step. The methanol which is provided to the esterification step can be obtained commercially, or can be recycled, for example from an MTBE splitting process as described above, or from the esterification itself. The methanol is optionally purified before being provided to the esterification.

It is preferred that the esterification of step c) is a liquid phase esterification. If the second oxidation stage in the catalytic reaction zone in step b) of the process according to the invention for preparation of methacrylic acid as described above is a liquid phase oxidation stage it is also possible that this second oxidation stage is combined with step ii) into a combined liquid phase oxidation-esterification stage.

The invention also relates to an apparatus for preparation of methyl methacrylate, comprising the apparatus according to the invention for production of a $C_4$ oxidation product, in fluid communication with
δ) an esterification unit.

The esterification unit is not particularly limited and can be any unit suitable for esterification to form methyl methacrylate. It is preferably suitable for liquid phase esterification. The esterification unit preferably comprises an esterification catalyst, which can be a heterogeneous or homogeneous catalyst such as a solid state catalyst or a liquid catalyst, and is preferably an acidic ion exchange resin such as those described in U.S. Pat. No. 6,469,292, JP 1249743, EP 1 254 887 A1 or commercially available under the trade names Amberlyst® (Rohm and Haas Corp.), Dowex®, (Dow Corp.) or Lewertit® (Lanxess AG), or an acid capable of catalysing esterification, such as sulphuric acid, $H_2SO_4$.

It is preferred in the apparatus described above that the esterification unit is in fluid communication with
ε) a supply for methanol.

The supply for methanol can comprise at least one of a supply for methanol obtained from splitting of MTBE and a supply for methanol obtained from another source, such as recycled unreacted methanol from the esterification reaction itself, or from a different reaction, or commercially obtained methanol. The supply for methanol can provide methanol to the apparatus upstream of or directly into the esterification unit. Where the methanol is obtained from splitting of MTBE and/or as recycled methanol from the esterification or from another reaction, the apparatus preferably further comprises a methanol purification unit between the source of methanol and the esterification unit, for example at least one of a distillation device, a wash device, an extraction device or a column, whereby at least one distillation device is preferred. An example of a purification unit for methanol is described in EP 1 254 887 A1.

The apparatus may further comprise a purification unit downstream of the esterification unit, preferably a purification unit for purification of methyl methacrylate. Suitable purification units are known to the person skilled in the art and preferably comprise at least one distillation device, crystalliser, extractor, column or wash device, more preferably at least one distillation device. This purification unit should enable the at least partial purification of methyl methacrylate and at least partial separation of side products, for example impurities arising from the esterification, unreacted methanol and/or methacrylic acid. Unreacted reagents can optionally be collected, or recycled into a process step, for example into the esterification reaction, optionally after being subjected to purification.

In a preferred embodiment of the process according to the invention for preparation of methyl methacrylate, said process is performed in an apparatus according to the invention.

The invention also relates to methyl methacrylate obtainable according to a process according to the invention.

The invention also relates to a process for preparation of a methacrylate ester with formula $[CH_2=C(CH_3)C(=O)O]_n$—R, comprising process steps
α1 preparation of methacrylic acid according to a process according to the present invention; or
α2 preparation of methyl methacrylate according to a process according to the present invention; and
α3 reaction of the methacrylic acid obtained in step α1 or of the methyl methacrylate obtained in step α2 with an alcohol of formula $R(OH)_m$,
whereby n and m represent an integer from 1 to 10, preferably from 1 to 6, more preferably from 1 to 5, more preferably from 1 to 4, more preferably from 1 to 3 and
R is selected from the group consisting of linear or branched, saturated or unsaturated, aliphatic or aromatic, ring or straight chain hydrocarbons and linear or branched, saturated or unsaturated, aliphatic or aromatic, ring or straight chain hetero-atom-comprising hydrocarbons, for example alkyls, hydroxyalkyls, aminoalkyls, other nitrogen- and/or oxygen-comprising residues, glycols, diols, triols, bisphenols, fatty acid residues, whereby R preferably represents butyl, in particular n-butyl, isobutyl, hydroxyethyl, preferably 2-hydroxyethyl, and hydroxpropyl, preferably 2-hydroxypropyl or 3-hydroxypropyl, ethyl, 2-ethylhexyl, isodecyl, cyclohexyl, isobornyl, benzyl, 3,3,5-trimethyl cyclohexyl, stearyl, dimethylaminoethyl, dimethylaminopropyl, 2-tert-butyl aminoethyl, ethyl triglycol, tetrahydrofurfuryl, butyl diglycol, methoxypolyethylene glycol-350, methoxypolyethylene glycol 500, methoxypolyethylene glycol 750, methoxypolyethylene glycol 1000, methoxypolyethylene glycol 2000, methoxypolyethylene glycol 5000, allyl, ethylene glycol, diethylene glycol, triethylene glycol, polyethylene glycol 200, polyethylene glycol 400, 1,3-butanediol, 1,4-butanediol, 1,6-hexanediol, glycerol, diurethane, ethoxylated bisphenol A, ethoxylated bisphenol A, for example with 10 ethylene oxide units; trimethylolpropane, an ethoxylated $C_{16}$-$C_{18}$ fatty alcohol such as, for example, with 25 ethylene oxide units, 2-trimethylammonium ethyl.

The methacrylate ester derivatives can be prepared in step α3 from methyl methacrylate by methods known to the skilled person, for example by transesterification. Alternatively, these derivatives may be prepared in step α3 by esterification of methacrylic acid according to the invention with the respective alcohol. In a further possible preparation of the hydroxyester derivatives, methacrylic acid according to the invention is reacted in a ring-opening reaction with a corresponding oxygen-comprising ring, for example an epoxide, in particular ethylene oxide or propylene oxide.

The invention also relates to a methacrylate ester with formula $[CH_2=C(CH_3)C(=O)O]_n$—R, wherein n and R are as defined above. Preferred methacrylate esters are alkyl methacrylates, in particular butyl methacrylates, in particular n-butyl methacrylate, isobutyl methacrylate, hydroxyester methacrylate derivatives, for example hydroxyethyl methacrylate, preferably 2-hydroxyethyl methacrylate, and hydroxypropyl methacrylate, preferably 2-hydroxypropyl methacrylate or 3-hydroxypropyl methacrylate, and special methacrylate esters ethyl methacrylate, 2-ethylhexyl methacrylate, isodecyl methacrylate, cyclohexyl methacrylate, isobornyl methacrylate, benzyl methacrylate, 3,3,5-trimethyl cyclohexyl methacrylate, stearyl methacrylate, dimethylaminoethyl methacrylate, dimethylaminopropyl methacrylate, 2-tert-butyl aminoethyl methacrylate, ethyl triglycol methacrylate, tetrahydrofurfuryl methacrylate, butyl diglycol methacrylate, methoxypolyethylene glycol-350 methacrylate, methoxypolyethylene glycol 500 methacrylate, methoxypolyethylene glycol 750 methacrylate, methoxypolyethylene glycol 1000 methacrylate, methoxypolyethylene glycol 2000 methacrylate, methoxypolyethylene glycol 5000 methacrylate, allyl methacrylate, a methacrylic ester of an ethoxylated (such as, for example, with 25 mol EO) $C_{16}$-$C_{18}$ fatty alcohol, 2-trimethylammonium ethyl methacrylate chloride; ethylene glycol dimethacrylate, diethylene glycol dimethacrylate, triethylene glycol dimethacrylate, polyethylene glycol 200 dimethacrylate, polyethylene glycol 400 dimethacrylate, 1,3-butanediol dimethacrylate, 1,4-butanediol dimethacrylate, 1,6-hexanediol dimethacrylate, glycerol dimethacrylate, diurethane dimethacrylate, ethoxylated bisphenol A dimethacrylate, ethoxylated (optionally with, for example, 10 EO) bisphenol A dimethacrylate; trimethylolpropane trimethacrylate.

The invention further relates to a process for producing a polymer comprising at least one monomer unit selected from methacrylic acid, methyl methacrylate and a methacrylic ester with formula $[CH_2=C(CH_3)C(=O)O]_n$—R, wherein n and R are as defined above, comprising the steps:

A1. preparation of at least one of methacrylic acid, methyl methacrylate and at least one methacrylate ester according to a process according to the invention, A2. polymerisation of
  A2a. at least one of the methacrylic acid, the methyl methacrylate and the at least one methacrylate ester obtained in step A1, and
  A2b. optionally at least one co-monomer which is co-polymerisable with at least one of methacrylic acid, methyl methacrylate and at least one methacrylate ester.

The polymerisation is not particularly limited and can be carried out by any method known to the skilled person and appearing suitable, for example as described in U.S. Pat. No. 5,292,797, U.S. Pat. No. 4,562,234, U.S. Pat. No. 5,773,505, U.S. Pat. No. 5,612,417, U.S. Pat. No. 4,952,455, U.S. Pat. No. 4,948,668, U.S. Pat. No. 4,239,671. Preferred polymerisation methods are radical polymerisation, initiated by initiators which decompose into radicals under the polymerisation conditions, whereby the polymerisation is preferably a solution or an emulsion polymerisation, preferably an aqueous solution polymerisation.

Examples of co-monomers are acrylamides and methacrylamides, acrylic acid esters and other acrylic acid esters and/or methacrylic acid esters, such as methyl acrylate, ethyl acrylate, propyl acrylate or butyl acrylate, ethyl methacrylate, propyl methacrylate or butyl methacrylate, as well as acetates such as vinyl acetate, styrene, butadiene and acrylonitrile. The at least one co-monomer is most preferably at least one co-monomer selected from the group consisting of: styrene, butadiene, acrylonitrile, butyl acrylate, vinyl acetate, methyl acrylate.

The polymerisation can also take place in the presence of one or more crosslinkers. Preferred cross-linkers according to the invention are compounds which have at least two ethylenically unsaturated groups in one molecule, compounds which have at least two functional groups which can react with functional groups of the monomers in a condensation reaction, in an addition reaction or a ring-opening reaction, compounds which have at least one ethylenically unsaturated group and at least one functional group which can react with functional groups of the monomers in a condensation reaction, an addition reaction or a ring-opening reaction, or polyvalent metal cations.

The invention also relates to a polymer obtainable according to a process according to the invention or comprising at least one monomer unit selected from a methacrylic acid monomer according to the invention or obtainable by a process according to the invention and a methyl methacrylate monomer according to the invention or obtainable by a process according to the invention and a methacrylate ester according to the invention or obtainable by a process according to the invention, as well as optionally other components such as a co-monomer and optionally a crosslinker.

The invention also relates to a process for producing a composition comprising at least a first component selected from at least one of methacrylic acid according to the invention, methyl methacrylate according to the invention, a methacrylate ester according to the invention, and a polymer comprising at least one monomer unit selected from methacrylic acid, methyl methacrylate and a methacrylate ester, comprising the steps:

B1. providing at least one first component selected from methacrylic acid according to the invention, methyl methacrylate according to the invention, a methacrylate ester according to the invention, and a polymer according to the invention comprising at least one monomer unit selected from methacrylic acid, methyl methacrylate and a methacrylate ester, B2. combining the at least one first component provided in B1 with at least one further component.

The at least one further component is preferably at least one component selected from natural or synthetic organic or inorganic polymers, for example selected from a substituted or unsubstituted polystyrene, poly-n-butyl acrylate, a polyacrylonitrile, a polysaccharide, a silica, and a nanomaterial.

The invention also relates to a composition comprising at least one first component selected from methacrylic acid according to the invention, methyl methacrylate according to the invention, a methacrylate ester according to the invention, and a polymer according to the invention comprising at least one monomer unit selected from methacrylic acid, methyl methacrylate and a methacrylate ester and at least one further component, or obtainable according to a process according to the invention.

It is preferred for the composition according to the invention that the at least one further component is at least one component selected from a substituted or unsubstituted polystyrene, poly-n-butyl acrylate, a polyacrylonitrile, a polysaccharide, a silica and a nanomaterial.

The invention also relates to chemical products such as a shaped article, a moulding material, a film, a sheet, a granulate, a composite, a foam, a fibre, a lubricant, an adhesive, a thickening agent, a suspending agent, a flocculant, a resin, a plastic, a coating, a contact lens, a construction material, an absorbent material, a pharmaceutical, a material for controlled release of active substances, a foam, a fibre, a lubricant, a powder or a particle comprising at least one of methacrylic acid according to the invention, methyl methacrylate according to the invention, methacrylate ester according to the invention, a polymer or co-polymer according to the invention which comprises methacrylic acid, methyl methacrylate, and/or a methacrylate ester, and a composition according to the invention.

The invention also relates to a use of at least one of methacrylic acid according to the invention, methyl methacrylate according to the invention, methacrylate ester according to the invention, a polymer or co-polymer according to the invention which comprises methacrylic acid, methyl methacrylate, and/or a methacrylate ester, and a composition according to the invention, in chemical products such as shaped articles, moulding materials, films, sheets, granulates, composites, adhesives, thickening agents, suspending agents, flocculants, resins, plastics, coatings, contact lenses, construction materials, absorbent materials, pharmaceuticals, materials for controlled release of active substances, foams, fibres, lubricants, powders, particles.

The invention is illustrated by non-limiting examples and exemplifying embodiments.

DESCRIPTION OF THE FIGURE

The FIGURE (FIG. 1) shows schematically an exemplifying embodiment of the apparatus 1 according to the invention.

A gaseous feed composition comprising at least two of isobutylene, MTBE, ETBE and TBA as feed compounds is provided to catalytic reaction zone 3 by means of at least two supplies 2, 2a, 2b and 2c, via control unit 4. MTBE or ETBE is provided from an MTBE or ETBE source respectively (not shown in the FIGURE) by means of supply 2a, or from splitter 7 by means of supply 2 or from both. isobutylene is provided from splitter 7 by means of supply 2 or from isobutylene evaporator 21 by means of supply 2b or from both. TBA is provided from splitter 7 by means of supply 2 or from TBA evaporator 22 by means of supply 2c or from both. Methanol can also be supplied if desired, by means of supply 2 from splitter 7, if splitter 7 is an MTBE splitter, or by means of a further supply (not depicted). Control unit 4 serves to regulate the flow of feed composition components towards catalytic reaction zone 3 and to regulate the constitution of the feed composition. The apparatus 1 can comprise one or more purification units 24 for the respective feed compounds upstream of catalytic reaction zone 3 or upstream of control unit 4 or upstream of isobutylene evaporator 21 and/or upstream of TBA evaporator 22, and downstream of MTBE splitter 7. From control unit 4, the feed composition flows into the first oxidation area 5 in catalytic reaction zone 3. Each oxidation area 5, 6, is supplied with air, steam and diluent by means of air supply 19, steam supply 20 and diluent supply 29 respectively. Diluent supply 29 is optionally supplied with diluent by means of diluent recycle flow 32 from quench unit 12 and/or purification unit 11, optionally via a combustion unit 33 (recycle flow 32 and combustion unit 33 are not shown for the sake of clarity). First oxidation area 5 comprises first oxidation catalyst 9 (not shown) in first oxidation reactor 8a. The gaseous feed composition is here subjected to catalytic gas phase oxidation to form methacrolein as main oxidation product in a first gaseous oxidation phase. The first oxidation phase then flows to second oxidation area 6a via optional quench area 30. Second oxidation area 6a comprises second oxidation catalyst 10a (not shown) in second oxidation reactor 8b. In second oxidation area 6a the first oxidation phase is subjected to a second catalytic gas phase oxidation to form mainly methacrylic acid as main oxidation product in a second gaseous oxidation phase. The second gaseous oxidation phase is then conducted to quench unit 12, where the methacrylic acid is condensed with a quenching agent to form a quench phase comprising methacrylic acid and impurities. Unreacted methacrolein is separated from the quenched second oxidation phase and can be recycled to second oxidation area 6a via methacrolein recycle conduit 23. The quench phase comprising methacrylic acid and impurities is then conducted to purification unit 11, where methacrylic acid is at least partially separated from the quenching agent and from the impurities. Methacrolein can also be separated in purification unit 11 and recycled via methacrolein recycle conduit 23. Purification unit 11 can include one or more purification stages, 11a, 11b, etc. (not shown in the FIGURE), depending on the desired degree of purity of methacrylic acid. The purified methacrylic acid can be collected from the purification unit via outlet 25. If the methacrylic acid is to be converted into methyl methacrylate, it can be conducted to esterification unit 14. Esterification unit 14 comprises an esterification catalyst 15 (not shown). Methanol is supplied to esterification unit 14 by means of methanol supply 16, whereby a methanol purification unit 17 can be located upstream of esterification unit 14. The methanol can be supplied from splitter 7, if this is an MTBE splitter, by means of methanol conduit 31, preferably via methanol purification unit 17, or from a different methanol source (not shown in the FIGURE). From esterification unit 14 the esterified reaction composition is conducted to purification unit 18, where the methyl methacrylate is separated from the reaction composition and from impurities. Purification unit 18 can comprise one or more purification stages 18a, 18b, etc. depending on the desired degree of purity of methyl methacrylate or on the impurities to be removed. Methyl methacrylate is recovered from purification unit 18 via outlet 26. Unreacted methanol exiting esterification unit 14 can also be separated in purification unit 18 and removed via methanol outlet 27, then recycled to esterification unit 14, optionally via methanol purification unit 17, or conducted away. Unreacted methacrylic acid exiting esterification unit 14 can also be separated in purification unit 18 and removed via methacrylic acid outlet 28, then recycled to esterification unit 14, optionally via methacrylic acid purification unit 11, or conducted away.

The catalytic reaction zone 3 illustrated in FIG. 1 as a two-stage oxidation zone can also be considered as a one-stage oxidation zone. In this embodiment, the purified isobutylene phase is conducted to catalytic reaction zone 3, comprising an oxidation area 5. In oxidation area 5, methacrolein is formed and converted continuously to methacrylic acid.

EXAMPLES

Examples 1 to 3

A feed composition is prepared with composition according to Table 1.

TABLE 1

|  | Example 1 | Example 2 | Example 3 |
|---|---|---|---|
| Isobutylene | 99.7 (Gew.-%) | 99.0 Gew.-% | 97.0 Gew.-% |
| tert-butyl alcohol | 0.1 ppm | 5.0 ppm | 0.75 Gew.-% |

$O_2$, $H_2O$ and diluent gases are added to the feed composition in the molar ratio given in Table 2.

TABLE 2

|  | Mol | Mol % |
| --- | --- | --- |
| IBEN (+tert-butyl alcohol) | 1 | 6 |
| $O_2$ | 2 | 13 |
| $N_2$ | 8 | 51 |
| $H_2O$ | 1.8 | 11 |
| $N_2/CO_2$ | 3 | 19 |

The resulting composition is then subjected to a first oxidation reactor, in which IBEN was oxidised to methacrolein according to the process and under the conditions of Example 15 of EP 0 807 465 A1.

To the first oxidation phase resulting from this first oxidation were then added $O_2$, $H_2O$ and diluent gases in molar amounts according to Table 3, based on the number of moles IBEN in the feed composition subjected to the first oxidation reactor.

TABLE 3

|  | Mol | Mol % |
| --- | --- | --- |
| $O_2$ | 1 | 5 |
| $N_2$ | 12 | 59 |
| $H_2O$ | 3.5 | 17 |
| $N_2/CO_2$ | 3 | 15 |

This feed was then subjected to a second oxidation reactor. In this second reactor, methacrolein was oxidised to methacrylic acid according to the process and under the conditions of Example 1 of EP 1 325 780 A1.

Yields of methacrylic acid were obtained according to Table 4, based on the number of moles of isobutylene introduced into the first oxidation reactor.

TABLE 4

| Example | Relative yield |
| --- | --- |
| 1 | 1.000 |
| 2 | 1.001 |
| 3 | 1.020 |

REFERENCE NUMERALS 1 apparatus
2 supplies
2a supply for methyl tert-butyl ether
2b supply for isobutylene
2c supply for tert-butyl alcohol
3 catalytic reaction zone
4 control unit
5 first oxidation area
6 further oxidation area
6a second oxidation area
7 splitter
8 oxidation reactor
8a first oxidation reactor
8b second oxidation reactor
9 first oxidation catalyst
10 further oxidation catalyst
10a second oxidation catalyst
11 purification unit
11a first purification stage
11b further purification stage
12 quench unit
13 purification unit for feed composition
14 esterification unit
15 esterification catalyst
16 supply for methanol
17 purification unit for methanol
18 purification unit for methyl methacrylate
18a first purification stage
18b further purification stage
19 supply for air
20 supply for water
21 isobutylene evaporator
22 tert-butyl alcohol evaporator
23 methacrolein recycle conduit
24 purification unit for feed compound
25 outlet for methacrylic acid
26 outlet for methyl methacrylate
27 outlet for methanol
28 outlet for methacrylic acid
29 supply for diluent
30 quench area
31 methanol conduit
32 diluent recycle flow
33 combustion unit

The invention claimed is:

1. A process for producing at least one $C_4$ oxidation product, comprising:
  a) providing a feed composition comprising at least two feed compounds selected from the group consisting of isobutylene, tert-butyl alcohol, methyl tert-butyl ether, and ethyl tert-butyl ether; and
  b) subjecting the feed composition to a catalytic reaction zone comprising at least one oxidation stage to obtain a reaction phase comprising at least one $C_4$ oxidation product,
  wherein the at least one oxidation stage comprises at least two oxidation stages separated by an intermediate area, and the at least two feed compounds of the feed composition comprise isobutylene as a main feed compound and at least one further feed compound in an amount of from 0.0005 to 5 wt. % based on a total weight of the at least two feed compounds in the feed composition.

2. The process according to claim 1, wherein the at least one $C_4$ oxidation product is at least one of methacrolein and methacrylic acid.

3. The process according to claim 1, wherein the at least one oxidation stage comprises a first oxidation stage and a second oxidation stage, a main product in a first $C_4$ oxidation phase of the first oxidation stage is methacrolein, and a main product of a second $C_4$ oxidation phase in the second oxidation stage is methacrylic acid.

4. The process according to claim 1, wherein the feed composition is provided before the first oxidation stage.

5. The process according to claim 1, wherein the feed composition comprises less than 70 mol % of methacrolein based on the feed composition.

6. The process according to claim 1, wherein at least the catalytic reaction occurs at least partially in a gas phase.

7. The process according to claim 1, further comprising
  c) working up the at least one $C_4$ oxidation product.

8. The process according to claim 1, wherein said process is performed in an apparatus comprising:
  α) at least two feed supplies;
  β) a catalytic reaction zone; and
  γ) at least one control unit configured to control the at least two feed supplies,
  wherein the at least two feed supplies are in fluid communication with the catalytic reaction zone.

9. A process for producing methyl methacrylate, comprising:
a) providing a feed composition comprising at least two feed compounds selected from the group consisting of isobutylene, tert-butyl alcohol, methyl tert-butyl ether, ethyl tert-butyl ether and methanol;
b) subjecting the feed composition to a catalytic reaction zone comprising at least one oxidation stage to obtain a reaction phase comprising at least one $C_4$ oxidation product selected from the group consisting of methacrolein and methacrylic acid; and
c) subjecting the reaction phase to esterification,
wherein the at least one oxidation stage comprises at least two oxidation stages separated by an intermediate area, and the at least two feed compounds of the feed composition comprise isobutylene as a main feed compound and at least one further feed compound in an amount of from 0.0005 to 5 wt. % based on a total weight of the at least two feed compounds in the feed composition.

10. The process according to claim 6, wherein said process is performed in an apparatus comprising:
α) at least two feed supplies;
β) a catalytic reaction zone;
γ) at least one control unit configured to control the at least two feed supplies; and
δ) an esterification unit,
wherein the at least two feed supplies are in fluid communication with the catalytic reaction zone.

11. A process for preparing a methacrylate ester, comprising:
preparing methacrylic acid or methyl methacrylate; and
reacting the methacrylic acid or the methyl methacrylate with an alcohol of formula $R(OH)_m$ to obtain a methacrylate ester having a formula $[CH_2=C(CH_3)C(=O)O]_n—R$,
wherein n and m represent an integer from 1 to 10,
R is selected from the group consisting of linear or branched, saturated or unsaturated, aliphatic or aromatic, ring or straight chain hydrocarbons and linear or branched, saturated or unsaturated, aliphatic or aromatic, ring or straight chain heteroatom-comprising hydrocarbons,
the methacrylic acid or the methyl methacrylate is prepared by a method comprising providing a feed composition comprising at least two feed compounds selected from the group consisting of isobutylene, tert-butyl alcohol, methyl tert-butyl ether, ethyl tert-butyl ether and methanol; and subjecting the feed composition to a catalytic reaction zone comprising at least two oxidation stages separated by an intermediate area, and the at least two feed compounds of the feed composition comprise isobutylene as a main feed compound and at least one further feed compound in an amount of from 0.0005 to 5 wt. % based on a total weight of the at least two feed compounds in the feed composition.

12. The process according to claim 1, wherein the at least two oxidation stages comprise a first oxidation stage and a second oxidation stage, the first oxidation stage is a gas phase oxidation stage, and the second oxidation stage is a liquid phase oxidation stage.

13. The process according to claim 1, wherein the at least two feed compounds of the feed composition comprise isobutylene as a main feed compound and at least one further feed compound in an amount of from 0.0010 to 5 wt. % based on a total weight of the at least two feed compounds in the feed composition.

14. The process according to claim 1, wherein the at least two feed compounds of the feed composition comprise isobutylene as a main feed compound and at least one further feed compound in an amount of from 0.0010 to 3 wt. % based on a total weight of the at least two feed compounds in the feed composition.

* * * * *